US012607634B2

(12) United States Patent
Xue et al.

(10) Patent No.: US 12,607,634 B2
(45) Date of Patent: Apr. 21, 2026

(54) METHODS AND COMPOSITIONS FOR ASSESSING IMMUNE RESPONSE IN MURINE TUMOR MODELS

(71) Applicant: CROWN BIOSCIENCE (SUZHOU) INC., Jiangsu (CN)

(72) Inventors: Jia Xue, Jiangsu (CN); Xiaobo Chen, Jiangsu (CN); Sheng Guo, Jiangsu (CN); Henry Li, Jiangsu (CN)

(73) Assignee: CROWN BIOSCIENCE (SUZHOU) INC., Suzhou (CN)

( * ) Notice: Subject to any disclaimer, the term of this patent is extended or adjusted under 35 U.S.C. 154(b) by 665 days.

(21) Appl. No.: 18/074,532

(22) Filed: Dec. 5, 2022

(65) Prior Publication Data

US 2023/0125549 A1    Apr. 27, 2023

Related U.S. Application Data

(63) Continuation of application No. PCT/CN2021/098547, filed on Jun. 7, 2021.

(30) Foreign Application Priority Data

Jun. 5, 2020    (WO) ................ PCT/CN2020/094595

(51) Int. Cl.
*G01N 33/574*        (2006.01)
*G01N 33/569*        (2006.01)

(52) U.S. Cl.
CPC . *G01N 33/57484* (2013.01); *G01N 33/56972* (2013.01)

(58) Field of Classification Search
None
See application file for complete search history.

(56) References Cited

U.S. PATENT DOCUMENTS

| | | |
|---|---|---|
| 2017/0028044 A1 | 2/2017 | Soon-Shiong et al. |
| 2018/0298450 A1 | 10/2018 | Minn et al. |
| 2019/0002986 A1 | 1/2019 | Reddy et al. |

FOREIGN PATENT DOCUMENTS

| | | |
|---|---|---|
| CN | 110055327 A | 7/2019 |
| CN | 110305965 A | 10/2019 |
| WO | 2019006427 A1 | 1/2019 |
| WO | 2019012105 A1 | 1/2019 |
| WO | 2020069501 A1 | 4/2020 |

OTHER PUBLICATIONS

Cesano, Journal for Immunotherapy vol. 3 Issue 1, 2015.*
International Search Report of PCT/CN2021/098547 mailed on Aug. 27, 2021.
Wen Zhang: "oHSV2 Can Target Murine Colon Carcinoma by Altering the Immune Status of the Tumor Microenvironment and Inducing Antitumor Immunity", Molecular Therapy—Oncolytics, vol. 16, Mar. 27, 2020 (Mar. 27, 2020), pp. 158-171, XP093164257.
Corail Total RNA-Seq Library Prep Kit, Lexogen, Feb. 28, 2019 (Feb. 28, 2019), pp. 1-36, XP093164615.
NCounter PanCancer Panels Collection, Nanostring, Jun. 30, 2018 (Jun. 30, 2018), pp. 1-4, XP093164249.
GeneChip Mouse Expression Set 430, Thermofisher, Dec. 31, 2009 (Dec. 31, 2009), pp. 1-2, XP093164639.
Cesano Alessandra et al: "nCounter PanCancer Immune Profiling Panel (NanoString Technologies, Inc., Seattle, WA)", Journal for Immunotherapy of Cancer, vol. 3, No. 1, Dec. 1, 2015 (Dec. 1, 2015), XP055908072.
Jong W. Yu: "Tumor-immune profiling of murine syngeneic tumor models as a framework to guide mechanistic studies and predict therapy response in distinct tumor microenvironments", PLOSONE, vol. 13, No. 11, Nov. 2, 2018 (Nov. 2, 2018), p. e0206223, XP093164253.
The Extended European Search Report of the EP counterpart application No. 21817904.2 mailed on Jun. 3, 2024.

* cited by examiner

*Primary Examiner* — Misook Yu
(74) *Attorney, Agent, or Firm* — JUNHE LAW OFFICE P. C.; Yi Zhang

(57)    ABSTRACT

The disclosure provides methods and compositions, e.g., kits and microarray, for assessing the immune response in a murine tumor model based on the expression of a gene panel that characterizes tumor immune interactions.

22 Claims, 5 Drawing Sheets

METHODS AND COMPOSITIONS FOR ASSESSING IMMUNE RESPONSE IN MURINE TUMOR MODELS

CROSS-REFERENCE TO RELATED APPLICATIONS

This application is a continuation of PCT/CN2021/098547 filed Jun. 7, 2021, which claims priority to application PCT/CN2020/094595, filed Jun. 5, 2020, the disclosure of which is incorporated herein by reference.

FIELD OF THE INVENTION

The present invention generally relates to molecular biology, cancer biology and animal models.

BACKGROUND

Cancer is a heterogenous disease and highly related to the immunological system. The significance of fully understanding the interactions between cancer and immunity in cancer therapeutics has been broadly noted, particularly for immune therapies. However, only 20-30% of cancer patients respond to immunotherapies and there is also the added complexity of inducing immune-related adverse effects and auto-immune reactions. Being able to predict who will benefit from immunotherapies could spare treatment costs and patient health.

Experimental murine models derived from a variety of biological technologies are essential preclinical model systems. Molecular pathology techniques, such as gene expression biomarkers, are widely used to systemically profile and characterize these models. So far, however, there has been no robust and cost-effective assay designed for murine preclinical immune-oncology research to characterize tumor-immune interactions at a gene expression level.

SUMMARY OF INVENTION

In one aspect, the present disclosure provides a method for assessing immune response in a murine model. In one embodiment, the method comprises: obtaining a sample from the murine model; detecting the expression level of a panel of genes in the sample, wherein the panel comprises at least 50 genes selected from the group disclosed herein; comparing the expression level of the panel to a reference expression level; and evaluating the immune response in the murine model.

In certain embodiments, the murine model has a tumor. In certain embodiments, the sample is a tumor tissue.

In certain embodiments, the murine model been treated with a therapy. In certain embodiments, the therapy is an immune therapy.

In certain embodiments, the expression of the panel of genes is detected using next-generation sequencing (NGS).

In certain embodiments, the immune response comprises activation of an immune cell selected from the group consisting of B-cell, dendritic cell, macrophage, monocyte, natural killer cell, CD4+ T cell and CD8+ T cell.

In another aspect, the present disclosure provides a kit for assessing immune response in a murine model. In certain embodiments, the kit comprises primers for detecting the expression of a panel of genes in a sample from the murine model, wherein the panel comprises at least 50 genes selected from the group disclosed herein.

In another aspect, the present disclosure provides a microarray for assessing immune response in a murine model. In certain embodiments, the microarray comprises probes for detecting the expression level of a panel of genes in a sample from the murine model, wherein the panel comprises at least 50 genes selected from the group disclosed herein.

In yet another aspect, the present disclosure provides a non-transitory computer readable medium having instructions stored thereon, wherein the instructions, when executed by a processor, cause the processor to: retrieving the expression level of a panel of genes in the sample, wherein the panel comprises at least 50 genes selected from the group disclosed herein; comparing the expression level of the panel to a reference expression level; and evaluating the immune response in the murine model.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1A:
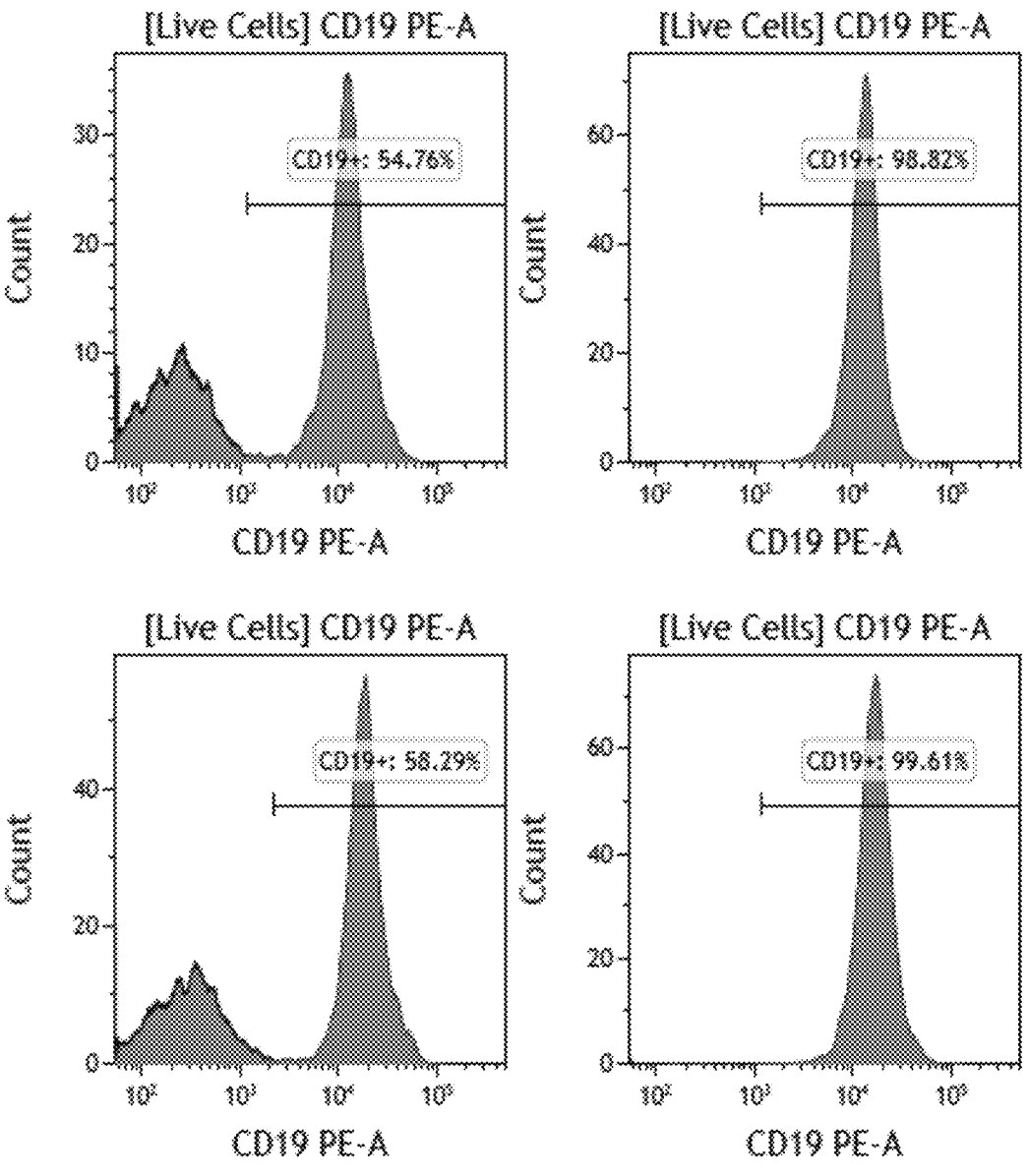
FIG. 1A-1B show the results of cell sorting for B cells (FIG. 1A) and T cells (FIG. 1B) from non-tumor bearing mice spleens from validation panel.
Figure 1B:
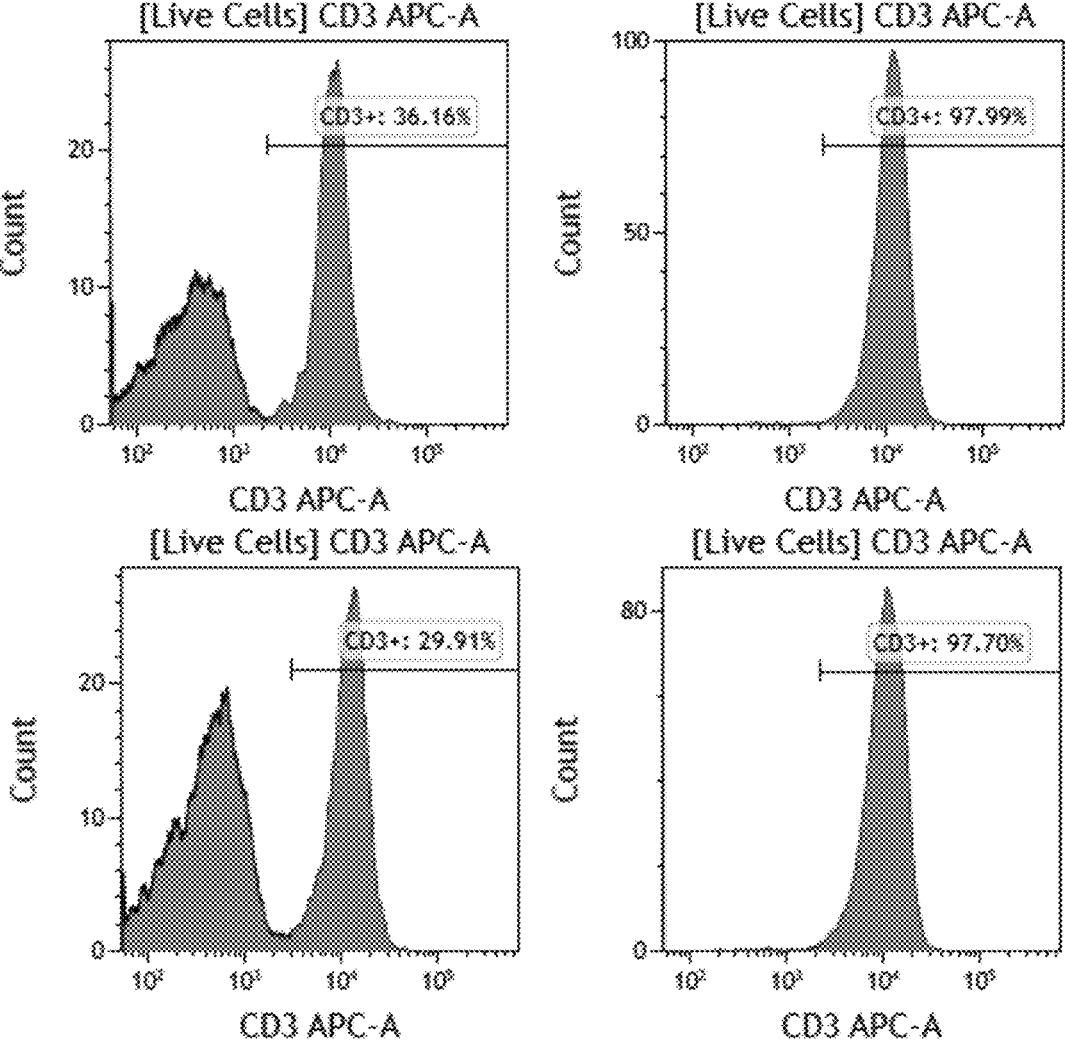

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

The term "amount" or "level" refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

As used herein, the term "cancer" or "tumor" refers to any diseases involving an abnormal cell growth and include all stages and all forms of the disease that affects any tissue, organ or cell in the body. The term includes all known cancers and neoplastic conditions, whether characterized as malignant, benign, soft tissue, or solid, and cancers of all stages and grades including pre- and post-metastatic cancers. In general, cancers can be categorized according to the tissue or organ from which the cancer is located or originated and morphology of cancerous tissues and cells. As used herein, cancer types include, without limitation, acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, leukaemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%>, 70%>, 80%>, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

The terms "determining," "assessing," "assaying," "measuring" and "detecting" can be used interchangeably and refer to both quantitative and semi-quantitative determinations. Where either a quantitative and semi-quantitative determination is intended, the phrase "determining a level" of a polynucleotide or polypeptide of interest or "detecting" a polynucleotide or polypeptide of interest can be used.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, microarray, Southern or northern hybridizations) are sequence dependent, and are different under different environmental parameters. An extensive guide to the hybridization of nucleic acids is found in, e.g., Tijssen *Laboratory Techniques in Biochemistry and Molecular Biology—Hybridization with Nucleic Acid Probes part I, Ch. 2, "Overview of principles of hybridization and the strategy of nucleic acid probe assays,"* (1993) Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell *Molecular Cloning: A Laboratory Manual* (3rd ed) Vol. 1-3 (2001) Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "murine model", as used herein a mouse used to study the development and progression of a disease or disorder, such as cancer, and to test treatments before they are given to human.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., as are well known in the art.

The term "sample" or "biological sample" used herein refers to any cell, tissue, organoid or any other sample that contains one or more nucleic acid molecule(s) of interest. In certain embodiments, the sample is a cell (e.g., normal cell, cancer cell, cell line), a tissue (e.g., a normal tissue, a cancer tissue, a xenograft or allograft tissue), an organoid, etc.

The term "substrate" when used in the context of an array refers to material capable of supporting associated assay components (e.g., assay regions, cells, test compounds, etc.). Examples of substrates include, but are not limited to glass, Si-based materials, functionalized polystyrene, functionalized polyethylene-glycol, functionalized organic polymers, nitrocellulose or nylon membranes, paper, cotton, and materials suitable for synthesis. Substrates need not be flat and include any type of shape including spherical shapes (e.g., beads). Materials attached to a substrate may be attached to any portion of the substrate (e.g., may be attached to an interior portion of a porous substrate material). Preferred embodiments of the present technology have nucleic acid probes attached to a substrate. A nucleic acid probe is "attached" to a substrate when it is associated with the substrate through a non-random chemical or physical interaction. In some preferred embodiments, the attachment is through a covalent bond, e.g., as provided by a linker.

The term "tumor sample" includes a biological sample or a sample from a biological source that contains one or more tumor cells. Biological samples include samples from body fluids, e.g., blood, plasma, serum, or urine, or samples derived, e.g., by biopsy, from cells, tissues or organs, preferably tumor tissue suspected to include or essentially consist of cancer cells.

Gene Panels for Assessing Immune Response

Malignant tumors do not only contain cancer cells. Normal cells form the body also infiltrate tumors. For example, a variety of immune cells infiltrating tumors can help detect and kill cancer cells, which has important impact on tumor progression and response to therapy. While gene expression levels are often studied in tumors, the proportion of different cell type, such as immune cells in the tumor, is rarely studied at the gene expression level.

The methods and compositions described herein are based, in part, on the discovery of a group of genes that can be used to identify and assess the immune response, such as the proportion of various immune cells in tumors. In certain embodiment, the tumors are obtained in a murine tumor model. In certain embodiments, the genes are selected based on the genomic data from non-tumor bearing mice as well as tumor bearing mice. In certain embodiments, the group of genes can be used to identify at least 8 different immune cell types, including B-cell, dendritic cell, macrophage, monocyte, natural killer cell, CD4+ T cell and CD8+ T cell. In certain embodiments, the group of genes covers surface markers and transcriptomic biomarkers for immune system, the key pathways at the interface of the tumor, tumor microenvironment, and immune response, as well as internal reference genes for data normalization.

In certain embodiments, the group of genes used herein are selected from the group as shown in Table 1.

Methods of Detecting the Expression Level of Gene Panel

In one aspect, the present disclosure provides a method for assessing immune response in a murine model. In certain embodiments, the method comprises: obtaining a sample from the murine model; detecting the expression level of a panel of genes in the sample, wherein the panel comprises at least 50, 100, 150, 200, 250, 300, 350, 400, 450, 500, 550, 600, 650, 700, 750, 800, 850, 900, 950, 1000 genes selected from the group as shown in Table 1; comparing the expression level of the panel to a reference expression level; and evaluating the immune response in the murine model.

In certain embodiments, the expression level of the gene panel can be detected in the RNA (e.g., mRNA) level using proper methods known in the art, including, without limitation, amplification assay, hybridization assay and sequencing assay.

Amplification Assay

A nucleic acid amplification assay involves copying a target nucleic acid (e.g. DNA or RNA), thereby increasing the number of copies of the amplified nucleic acid sequence. Amplification may be exponential or linear. Exemplary nucleic acid amplification methods include, but are not limited to, amplification using the polymerase chain reaction ("PCR", see U.S. Pat. Nos. 4,683,195 and 4,683,202; PCR Protocols: A Guide To Methods And Applications (Innis et al., eds, 1990)), reverse transcriptase polymerase chain reaction (RT-PCR), quantitative real-time PCR (qRT-PCR); quantitative PCR, such as TaqMan®, nested PCR, ligase chain reaction (See Abravaya, K., et al., Nucleic Acids Research, 23:675-682, (1995), branched DNA signal amplification (see, Urdea, M. S., et al., AIDS, 7 (suppl 2):S11-S14, (1993), amplifiable RNA reporters, Q-beta replication (see Lizardi et al., *Biotechnology* (1988) 6: 1197), transcription-based amplification (see, Kwoh et al., *Proc. Natl. Acad. Sci. USA* (1989) 86: 1173-1177), boomerang DNA amplification, strand displacement activation, cycling probe technology, self-sustained sequence replication (Guatelli et al., *Proc. Natl. Acad. Sci. USA* (1990) 87:1874-1878), rolling circle replication (U.S. Pat. No. 5,854,033), isothermal nucleic acid sequence based amplification (NASBA), and serial analysis of gene expression (SAGE).

In certain embodiments, the nucleic acid amplification assay is a PCR-based method. PCR is initiated with a pair of primers that hybridize to the target nucleic acid sequence to be amplified, followed by elongation of the primer by polymerase which synthesizes the new strand using the target nucleic acid sequence as a template and dNTPs as building blocks. Then the new strand and the target strand are denatured to allow primers to bind for the next cycle of extension and synthesis. After multiple amplification cycles, the total number of copies of the target nucleic acid sequence can increase exponentially. When the nucleic acid obtained from a sample is RNA, the amplification step may optionally comprise a reverse transcription step to produce cDNA of the RNA in the sample. The cDNA is then amplified using the primers to allow detection of expression level of the genes of interest.

In certain embodiments, intercalating agents that produce a signal when intercalated in double stranded DNA may be used. Exemplary agents include SYBR GREEN™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In certain embodiments, a detectably labeled primer or a detectably labeled probe can be used, to allow detection of the mRNA (or cDNA reverse transcribed from mRNA) of the gene of interest corresponding to that primer or probe. In certain embodiments, multiple labeled primers or labeled probes with different detectable labels can be used to allow simultaneous detection of the expression of multiple gene of interest.

Hybridization Assay

Nucleic acid hybridization assays use probes to hybridize to the target nucleic acid, thereby allowing detection of the target nucleic acid. Non-limiting examples of hybridization assay include Northern blotting, Southern blotting, in situ hybridization, microarray analysis, and multiplexed hybridization-based assays.

In certain embodiments, the probes for hybridization assay are detectably labeled. In certain embodiments, the nucleic acid-based probes for hybridization assay are unlabeled. Such unlabeled probes can be immobilized on a solid support, such as a microarray, and can hybridize to the target nucleic acid molecules which are detectably labeled.

In certain embodiments, hybridization assays can be performed by isolating the nucleic acids (e.g., RNA or DNA), separating the nucleic acids (e.g., by gel electrophoresis) followed by transfer of the separated nucleic acid on suitable membrane filters (e.g. nitrocellulose filters), where the probes hybridize to the target nucleic acids and allows detection. See, for example, Molecular Cloning: A Laboratory Manual, J. Sambrook et al., eds., 2nd edition, Cold Spring Harbor Laboratory Press, 1989, Chapter 7. The hybridization of the probe and the target nucleic acid can be detected or measured by methods known in the art. For example, autoradiographic detection of hybridization can be performed by exposing hybridized filters to photographic film.

In some embodiments, hybridization assays can be performed on microarrays. Microarrays provide a method for the simultaneous measurement of the levels of large numbers of target nucleic acid molecules. The target nucleic acids can be RNA, DNA, cDNA reverse transcribed from mRNA, or chromosomal DNA. The target nucleic acids can be allowed to hybridize to a microarray comprising a substrate having multiple immobilized nucleic acid probes arrayed at a density of up to several million probes per square centimeter of the substrate surface. The RNA or DNA in the sample is hybridized to complementary probes on the array and then detected by laser scanning. Hybridization intensities for each probe on the array are determined and converted to a quantitative value representing relative levels of the RNA or DNA. See, U.S. Pat. Nos. 6,040,138, 5,800, 992 and 6,020,135, 6,033,860, and 6,344,316.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992. Arrays may be packaged in such a manner as to allow for diagnostics or other manipulation of an all-inclusive device. Useful microarrays are also commercially available, for example, microarrays from Affymetrix, from Nano String Technologies, QuantiGene 2.0 Multiplex Assay from Panomics.

Sequencing Methods

Sequencing methods useful in the measurement of the expression of the gene panel involves sequencing of the target nucleic acid. Any sequencing known in the art can be used to detect the expression of the gene of interest. In general, sequencing methods can be categorized to traditional or classical methods and high throughput sequencing (next generation sequencing). Traditional sequencing methods include Maxam-Gilbert sequencing (also known as chemical sequencing) and Sanger sequencing (also known as chain-termination methods).

High throughput sequencing, or next generation sequencing, by using methods distinguished from traditional methods, such as Sanger sequencing, is highly scalable and able to sequence the entire genome or transcriptome at once. High throughput sequencing involves sequencing-by-synthesis, sequencing-by-ligation, and ultra-deep sequencing (such as described in Marguiles et al., *Nature* 437 (7057): 376-80 (2005)). Sequence-by-synthesis involves synthesizing a complementary strand of the target nucleic acid by incorporating labeled nucleotide or nucleotide analog in a polymerase amplification. Immediately after or upon successful incorporation of a label nucleotide, a signal of the label is measured and the identity of the nucleotide is recorded. The detectable label on the incorporated nucleotide is removed before the incorporation, detection and identification steps are repeated. Examples of sequence-by-synthesis methods are known in the art, and are described for example in U.S. Pat. Nos. 7,056,676, 8,802,368 and 7,169, 560, the contents of which are incorporated herein by reference. Sequencing-by-synthesis may be performed on a solid surface (or a microarray or a chip) using fold-back PCR and anchored primers. Target nucleic acid fragments can be attached to the solid surface by hybridizing to the anchored primers, and bridge amplified. This technology is used, for example, in the Illumina® sequencing platform.

Pyrosequencing involves hybridizing the target nucleic acid regions to a primer and extending the new strand by sequentially incorporating deoxynucleotide triphosphates corresponding to the bases A, C, G, and T (U) in the presence of a polymerase. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined.

In certain embodiments, the expression of the genes of interest is detected by whole transcriptome shotgun sequencing (RNA sequencing). The method of RNA sequencing has been described (see Wang Z, Gerstein M and Snyder M, *Nature Review Genetics* (2009) 10:57-63; Maher C A et al., *Nature* (2009) 458:97-101; Kukurba K & Montgomery S B, Cold Spring Harbor Protocols (2015) 2015(11): 951-969). In certain embodiment, samples subject to the RNA sequencing are pre-treated to enrich the expression product of the genes of interest, e.g., using oligonucleotide-based hybridization/ capture techniques. In certain embodiments, the probes used in the hybridization/capture techniques have a length ranging from 20-200 nucleotides, 20-500 nucleotides, 20-1000 nucleotides, 20-2000 nucleotides, 20-5000 nucleotides, or 20-7000 nucleotides.

Comparing with a Reference Level

In certain embodiments, the methods disclosed herein include a step of comparing the detected expression level of the gene panel to a reference expression level.

The term "reference expression level" refers to a level of expression that is representative of a reference sample. In certain embodiments, the reference sample is obtained from a healthy (e.g., non-tumor bearing) subject or tissue. In certain embodiments, the reference sample is a cancer or tumor tissue. In certain embodiments, the reference sample is obtained from a subject or tissue in which the immune response is activated, e.g., by the tumor or therapeutics (e.g., treated by an anti-tumor therapy, e.g., an anti-immune checkpoint antibody, such as anti-PD-1, anti-PD-L1). In certain embodiments, the reference expression level is obtained using the same or comparable measurement method or assay as used in the detection of the expression level of the target gene in the test sample.

In certain embodiments, the reference expression level can be predetermined. For example, the reference expression level can be calculated or generalized based on measurements of the expression level of the target gene in a collection of general cancer or tumor samples or tissues from a tumor of the same type. For another example, the reference expression level can be based on statistics of the expression level of the target gene generally observed in an average cancer or tumor samples from a general cancer or tumor population.

In certain embodiments, the comparing step in the method provided herein involves determining the difference between the detected expression level and the reference expression level. The difference from the reference expression level can be elevation or reduction.

In certain embodiments, the difference from the reference expression level is further compared with a threshold. In certain embodiments, a threshold can be set by statistical methods, such that if the difference from the reference expression level reaches the threshold, such difference can be considered statistically significant. Useful statistical analysis methods are described in L. D. Fisher & G. van-Belle, Biostatistics: A Methodology for the Health Sciences (Wiley-Interscience, N Y, 1993). Statistically significance can be determined based on confidence ("p") values, which can be calculated using an unpaired 2-tailed t test. A p value less than or equal to, for example, 0.1, 0.05, 0.025, or 0.01 usually can be used to indicated statistical significance.

Confidence intervals and p-values can be determined by methods well-known in the art. See, e.g., Dowdy and Wearden, Statistics for Research, John Wiley & Sons, New York, 1983.

Evaluation of Anti-Tumor Therapy

In another aspect, the present disclosure further provides a method to evaluate a treatment in a murine model based on the expression level of a panel of genes as disclosed herein. In certain embodiments, the method comprises administering a treatment to a murine model; obtaining a sample from the murine model; detecting the expression level of a panel of genes in the sample, wherein the panel comprises at least 50 genes selected from the group as shown in Table 1; comparing the expression level of the panel to a reference expression level; and evaluating the immune response in the murine model.

In certain embodiments, the treatment involves an anti-hormonal agent, including natural or synthetic organic or peptide compounds that act to regulate or inhibit hormone action on tumors.

In certain embodiments, the treatment involves an angiogenesis inhibitor, including VEGFR inhibitors, integrin receptor antagonists and integrin antagonists.

In certain embodiments, the treatment involves a tumor cell pro-apoptotic or apoptosis-stimulating agent.

In certain embodiments, the treatment involves a signal transduction inhibitor, such as an erbB2 receptor inhibitors, inhibitors of other protein tyrosine-kinases; ras inhibitors; raf inhibitors; MEK inhibitors; mTOR inhibitors; cyclin dependent kinase inhibitors; protein kinase C inhibitors; and PDK-1 inhibitors.

In certain embodiments, the treatment involves an anti-proliferative agent. Anti-proliferative agents include, for example: inhibitors of the enzyme farnesyl protein transferase and inhibitors of the receptor tyrosine kinase PDGFR.

In certain embodiments, the treatment involves a cancer immunotherapy agent, such as an antibody specifically binding to an immune checkpoint. Immune checkpoints include, for example: A2AR, B7.1, B7.2, B7-H2, B7-H3, B7-H4, B7-H6, BTLA, CD48, CD160, CD244, CTLA-4, ICOS, LAG-3, LILRB1, LILRB2, LILRB4, OX40, PD-1, PD-L1, PD-L2, SIRPalpha (CD47), TIGIT, TIM-3, TIM-1, TIM-4, and VISTA.

Kits and Microarrays

In another aspect, the present disclosure provides kits for use in the methods described above. The kits may comprise any or all of the reagents to perform the methods described herein. In certain embodiments, the kit comprises primers for detecting the expression of a panel of genes in a sample from the murine model. In certain embodiments, the panel comprises at least 50, 100, 150, 200, 250, 300, 350, 400, 450, 500, 550, 600, 650, 700, 750, 800, 850, 900, 950, 1000 genes selected from the group as shown in Table 1.

In certain embodiments, the kit further comprises an agent for amplifying the expression product, e.g., mRNA, of the gene panel using the primers. In addition, the kits may include instructional materials containing directions (i.e., protocols) for the practice of the methods provided herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In another aspect, the present disclosure provides oligonucleotide probes for detecting the expression level of a panel of genes in a sample from the murine model. In certain embodiments, the panel comprises at least 50, 100, 150, 200, 250, 300, 350, 400, 450, 500, 550, 600, 650, 700, 750, 800, 850, 900, 950, 1000 genes selected from the group as shown in Table 1.

In certain embodiments, the probes are attached to a solid support, such as an array slide or chip, e.g., as described in Eds., Bowtell and Sambrook DNA Microarrays: A Molecular Cloning Manual (2003) Cold Spring Harbor Laboratory Press. Construction of such devices are well known in the art, for example as described in US patents and patenttent Publications U.S. Pat. No. 5,837,832; PCT application WO95/11995; U.S. Pat. Nos. 5,807,522; 7,157,229, 7,083, 975, 6,444,175, 6,375,903, 6,315,958, 6,295,153, and 5,143, 854, 2007/0037274, 2007/0140906, 2004/0126757, 2004/ 0110212, 2004/0110211, 2003/0143550, 2003/0003032, and 2002/0041420. Nucleic acid arrays are also reviewed in the following references: Biotechnol Annu Rev (2002) 8:85-101; Sosnowski et al. Psychiatr Genet (2002)12(4): 181-92; Heller, Annu Rev Biomed Eng (2002) 4: 129-53; Kolchinsky et al., Hum. Mutat (2002) 19(4):343-60; and McGail et al., Adv Biochem Eng Biotechnol (2002) 77:21-42.

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of arrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may also be nucleic acids on beads, gels, polymeric surfaces, fibers such as fiber optics, glass or any other appropriate substrate, see U.S. Pat. Nos. 5,770,358, 5,789,162, 5,708, 153, 6,040,193 and 5,800,992. Arrays may be packaged in such a manner as to allow for diagnostics or other manipulation of an all-inclusive device.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, Tetrahedron Letts. (1981) 22: 1859-1862, using an automated synthesizer, as described in Needham-Van Devanter et al, Nucleic Acids Res. (1984) 12:6159-6168.

Computer-Implemented Methods, Systems and Devices

Any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps.

Although presented as numbered steps, steps of methods herein can be performed at a same time or in a different order. Additionally, portions of these steps may be used with portions of other steps from other methods. Also, all or portions of a step may be optional. Any of the steps of any of the methods can be performed with modules, circuits, or other means for performing these steps.

Any of the computer systems mentioned herein may utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. The subsystems can be interconnected via a system bus. Additional subsystems include, for examples, a printer, keyboard, storage device(s), monitor, which is coupled to display adapter, and others. Peripherals and input/output (I/O) devices, which couple to I/O controller, can be connected to the computer system by any number of means known in the art, such as serial port. For example, serial port or external interface (e.g., Ethernet, Wi-Fi, etc.) can be used to connect computer system to a wide area network such as the Internet, a mouse input device, or a scanner. The interconnection via system bus allows the central processor to communicate with each subsystem and to control the execution of instructions from system memory or the storage device(s) (e.g., a fixed disk, such as a hard drive or optical disk), as well as the exchange of information between subsystems. The system memory and/or the storage device(s) may embody a computer readable medium. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g., an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1

Figure 2:
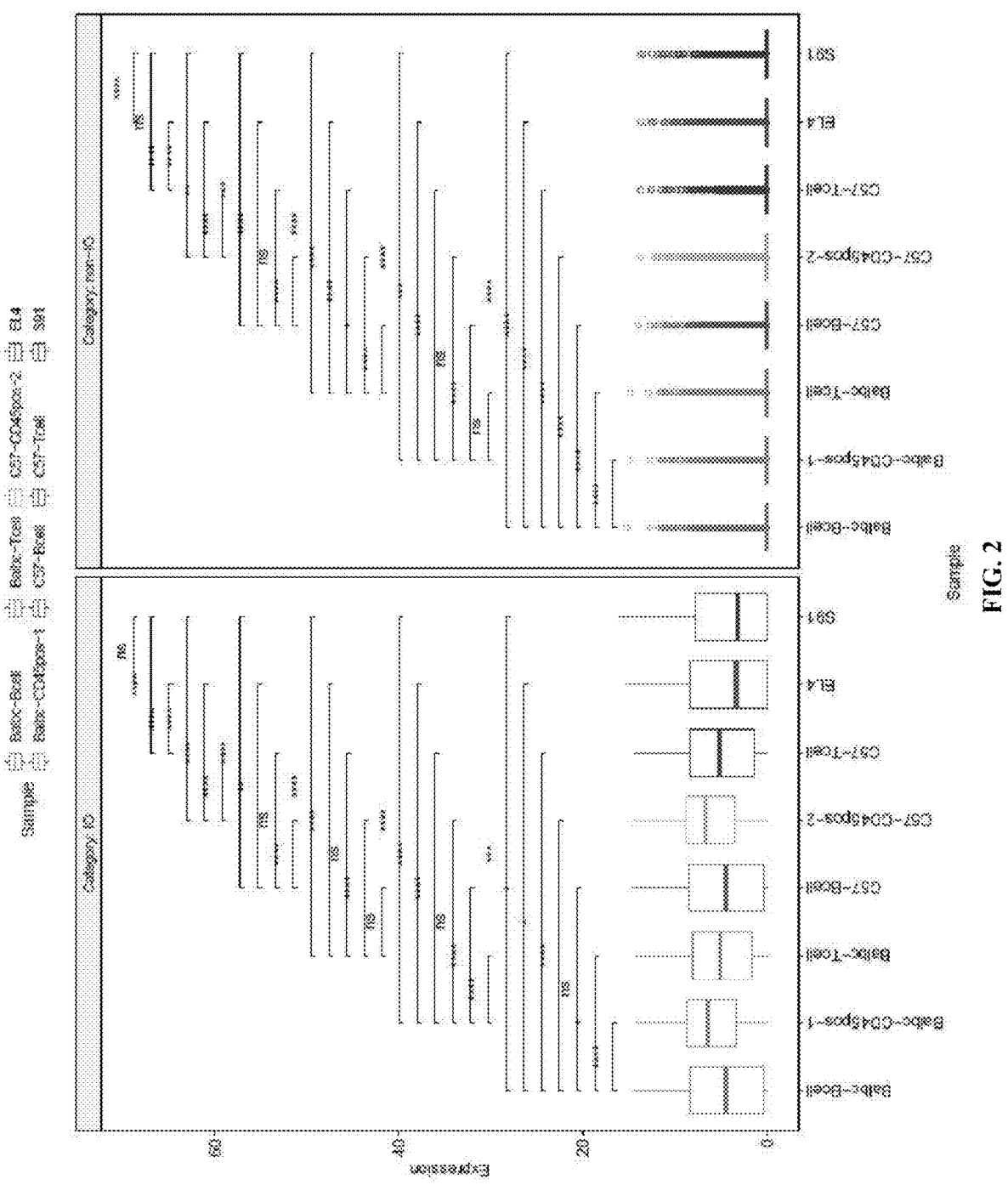
FIG. 2 shows the quality assessment by comparing murine immune-oncology panel target gene and non-target gene expression levels in validation panels.
Figure 3:
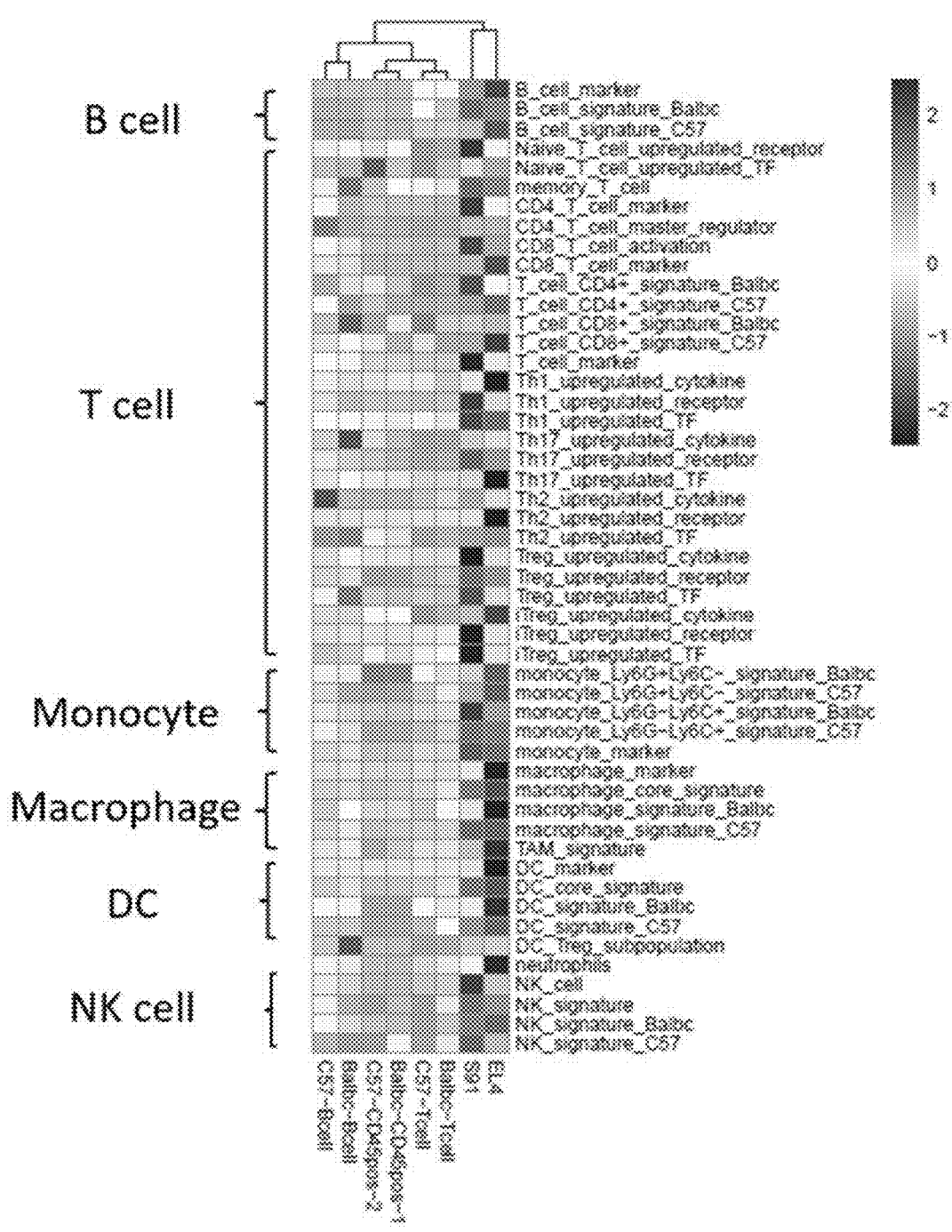
FIG. 3 shows the single-sample gene set enrichment analysis (ssGSEA) on murine immune-oncology panel signatures grouped in 50 categories demonstrates high consistency of biomarkers in validation panels.
Figure 4:
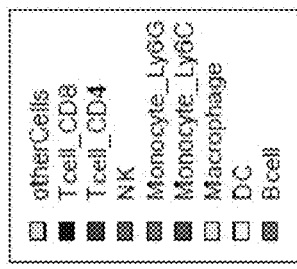
FIG. 4 show the estimated cell fractions in validation panels using murine pan-cancer gene expression panel-based signatures.

This example illustrates the identification of murine pan-cancer gene expression panel for immuno-oncology and tumor microenvironment studies Materials and Methods Marker genes were identified by combining public and in-house reference genomic data for non-tumor bearing mice as well as tumor-bearing mouse models. Oligonucleotide-based hybridization/capture techniques, analogous to exome sequencing of targeting specific regions, are established on Illumina Novaseq and BGI MGIseq platforms. The results were further verified using PCR assays and eight control panels with murine immune cells and tumor cell lines.
Results Based on the immune signature analysis, the inventors selected 1080 genes (see Table 1) that cover surface markers and transcriptomic biomarkers for immune system, the key pathways at the interface of the tumor, tumor microenvironment, and immune response, as well as internal reference genes for data normalization. The validation panels showed good consistency of gene expression in respective cell types (see FIGS. 2 and 3). The inventors also estimated the cell fractions in validation panels based on the expression of the gene panel (see FIG. 4).

The murine immune-oncology NGS panel can be used to characterize tumor-immune interactions more efficiently and in a cost-effective manner for preclinical studies, which will provide an enhanced insight into the tumor microenvironment, especially following treatment with immuno-therapy, with high-content data that has the potential to better understand the lack of response versus response, which ultimately could translate more effectively into the clinic as well as for early identification of immunotherapy companion diagnostics.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

TABLE 1

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000030724 | Cd19 | ENSMUSG00000036887 | C1qa |
| ENSMUSG00000026447 | Pik3c2b | ENSMUSG00000036856 | Wnt4 |
| ENSMUSG00000026616 | Cr2 | ENSMUSG00000058908 | Pla2g2a |
| ENSMUSG00000020183 | Cpm | ENSMUSG00000028914 | Casp9 |
| ENSMUSG00000095105 | Edaradd | ENSMUSG00000028599 | Tnfrsf1b |
| ENSMUSG00000051022 | Hs3st1 | ENSMUSG00000028602 | Tnfrsf8 |
| ENSMUSG00000005540 | Fcer2a | ENSMUSG00000028991 | Mtor |
| ENSMUSG00000044694 | 2010007H06Rik | ENSMUSG00000039936 | Pik3cd |
| ENSMUSG00000002007 | Srpk3 | ENSMUSG00000063524 | Eno1 |
| ENSMUSG00000079445 | B3gnt7 | ENSMUSG00000028965 | Tnfrsf9 |
| ENSMUSG00000057337 | Chst3 | ENSMUSG00000024793 | Tnfrsf25 |
| ENSMUSG00000057098 | Ebf1 | ENSMUSG00000042333 | Tnfrsf14 |
| ENSMUSG00000017400 | Stac2 | ENSMUSG00000029075 | Tnfrsf4 |
| ENSMUSG00000001027 | Scn4a | ENSMUSG00000041954 | Tnfrsf18 |
| ENSMUSG00000104213 | Ighd | ENSMUSG00000035692 | Isg15 |
| ENSMUSG00000022416 | Cacna1i | ENSMUSG00000040274 | Cdk6 |
| ENSMUSG00000042514 | Klhl14 | ENSMUSG00000002944 | Cd36 |
| ENSMUSG00000037071 | Scd1 | ENSMUSG00000042453 | Rein |
| ENSMUSG00000050556 | Kcnb1 | ENSMUSG00000025746 | Il6 |
| ENSMUSG00000014030 | Pax5 | ENSMUSG00000025747 | Tyms |
| ENSMUSG00000052271 | Bhlha15 | ENSMUSG00000029145 | Eif2b4 |
| ENSMUSG00000071226 | Cecr2 | ENSMUSG00000029084 | Cd38 |
| ENSMUSG00000030256 | Bhlhe41 | ENSMUSG00000029086 | Prom1 |
| ENSMUSG00000030313 | Dennd5b | ENSMUSG00000044827 | Tlr1 |
| ENSMUSG00000023274 | Cd4 | ENSMUSG00000062960 | Kdr |
| ENSMUSG00000001444 | Tbx21 | ENSMUSG00000029371 | Cxcl5 |
| ENSMUSG00000015619 | Gata3 | ENSMUSG00000029373 | Pf4 |
| ENSMUSG00000028150 | Rorc | ENSMUSG00000029379 | Cxcl3 |
| ENSMUSG00000039521 | Foxp3 | ENSMUSG00000029375 | Cxcl15 |
| ENSMUSG00000026011 | Ctla4 | ENSMUSG00000029380 | Cxcl1 |
| ENSMUSG00000057329 | Bcl2 | ENSMUSG00000058427 | Cxcl2 |
| ENSMUSG00000026581 | Sell | ENSMUSG00000029378 | Areg |
| ENSMUSG00000019982 | Myb | ENSMUSG00000029417 | Cxcl9 |
| ENSMUSG00000048756 | Foxo3 | ENSMUSG00000060183 | Cxcl11 |
| ENSMUSG00000038151 | Prdm1 | ENSMUSG00000023078 | Cxcl13 |
| ENSMUSG00000037868 | Egr2 | ENSMUSG00000046709 | Mapk10 |
| ENSMUSG00000019942 | Cdk1 | ENSMUSG00000042190 | Cmklr1 |
| ENSMUSG00000044199 | S1pr4 | ENSMUSG00000041827 | Oasl1 |
| ENSMUSG00000020297 | Nsg2 | ENSMUSG00000029556 | Hnf1a |
| ENSMUSG00000054404 | Slfn5 | ENSMUSG00000029602 | Rasal1 |
| ENSMUSG00000020644 | Id2 | ENSMUSG00000032690 | Oas2 |
| ENSMUSG00000015437 | Gzmb | ENSMUSG00000032661 | Oas3 |
| ENSMUSG00000022346 | Myc | ENSMUSG00000052776 | Oas1a |
| ENSMUSG00000075602 | Ly6a | ENSMUSG00000043733 | Ptpn11 |
| ENSMUSG00000000028 | Cdc45 | ENSMUSG00000025534 | Gusb |
| ENSMUSG00000026872 | Zeb2 | ENSMUSG00000049551 | Fzd9 |
| ENSMUSG00000027720 | Il2 | ENSMUSG00000070464 | Ccl26 |
| ENSMUSG00000045092 | S1pr1 | ENSMUSG00000004814 | Ccl24 |
| ENSMUSG00000062585 | Cnr2 | ENSMUSG00000025856 | Pdgfa |
| ENSMUSG00000007872 | Id3 | ENSMUSG00000079109 | Pms2 |
| ENSMUSG00000029178 | Klf3 | ENSMUSG00000029648 | Flt1 |
| ENSMUSG00000030103 | Bhlhe40 | ENSMUSG00000066551 | Hmgb1 |
| ENSMUSG00000030156 | Cd69 | ENSMUSG00000041147 | BrCa2 |
| ENSMUSG00000055148 | Klf2 | ENSMUSG00000009376 | Met |
| ENSMUSG00000032294 | Pkm | ENSMUSG00000010797 | Wnt2 |
| ENSMUSG00000052336 | Cx3cr1 | ENSMUSG00000029771 | Irf5 |
| ENSMUSG00000050232 | Cxcr3 | ENSMUSG00000057137 | Tmem140 |
| ENSMUSG00000053977 | Cd8a | ENSMUSG00000038507 | Parp12 |
| ENSMUSG00000003134 | Tbc1d8 | ENSMUSG00000029915 | Clec5a |
| ENSMUSG00000054702 | Ap1s3 | ENSMUSG00000029687 | Ezh2 |
| ENSMUSG00000038179 | Slamf7 | ENSMUSG00000054435 | Gimap4 |
| ENSMUSG00000039783 | Kmo | ENSMUSG00000047867 | Gimap6 |
| ENSMUSG00000004665 | Cnn2 | ENSMUSG00000029798 | Herc6 |
| ENSMUSG00000000861 | Bcl11a | ENSMUSG00000025889 | Snca |
| ENSMUSG00000011256 | Adam19 | ENSMUSG00000049093 | Il23r |
| ENSMUSG00000037944 | Ccr7 | ENSMUSG00000053044 | Cd8b1 |
| ENSMUSG00000047415 | Gpr68 | ENSMUSG00000030045 | Mrpl19 |
| ENSMUSG00000021298 | Gpr132 | ENSMUSG00000000628 | Hk2 |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000022504 | Ciita | E NSM USG00000034245 | Hdac11 |
| ENSMUSG00000052013 | Btla | ENSMUSG00000033933 | Vhl |
| ENSMUSG00000067341 | H2-Eb2 | ENSMUSG00000000440 | Pparg |
| ENSMUSG00000073409 | H2-Q6 | ENSMUSG00000061353 | Cxcl12 |
| ENSMUSG00000000673 | Haao | ENSMUSG00000030170 | Wnt5b |
| ENSMUSG00000024789 | Jak2 | ENSMUSG00000004446 | Bid |
| ENSMUSG00000076441 | Ass1 | ENSMUSG00000030111 | A2m |
| ENSMUSG00000026875 | Traf1 | ENSMUSG00000030142 | Clec4e |
| ENSMUSG00000035000 | Dpp4 | ENSMUSG00000008845 | Cd163 |
| ENSMUSG00000027583 | Zbtb46 | ENSMUSG00000023456 | Tpi1 |
| ENSMUSG00000070691 | Runx3 | ENSMUSG00000030124 | Lag3 |
| ENSMUSG00000039899 | Fgl2 | ENSMUSG00000038213 | Tapbpl |
| ENSMUSG00000005672 | Kit | ENSMUSG00000030336 | Cd27 |
| ENSMUSG00000037905 | Bri3bp | ENSMUSG00000000184 | Ccnd2 |
| ENSMUSG00000042817 | Flt3 | ENSMUSG00000079299 | Klrb1 |
| ENSMUSG00000067610 | Klri1 | ENSMUSG00000079293 | Clec7a |
| ENSMUSG00000074227 | Spint2 | ENSMUSG00000030162 | Olr1 |
| ENSMUSG00000039062 | Anpep | ENSMUSG00000030165 | Klrd1 |
| ENSMUSG00000030643 | Rab30 | ENSMUSG00000079853 | Klra1 |
| ENSMUSG00000006362 | Cbfa2t3 | ENSMUSG00000030246 | Ldhb |
| ENSMUSG00000032322 | Pstpip1 | ENSMUSG00000030268 | Bcat1 |
| ENSMUSG00000066456 | Hmgn3 | ENSMUSG00000030265 | Kras |
| ENSMUSG00000047678 | Gpr82 | ENSMUSG00000058818 | Pirb |
| ENSMUSG00000050921 | P2ry10 | ENSMUSG00000055541 | Lair1 |
| ENSMUSG00000052688 | Rab7b | ENSMUSG00000070873 | Lilra5 |
| ENSMUSG00000034675 | Dbn1 | ENSMUSG00000004371 | Il11 |
| ENSMUSG00000025279 | Dnase1l3 | ENSMUSG00000049130 | C5ar1 |
| ENSMUSG00000090877 | Hspa1b | ENSMUSG00000002083 | Bbc3 |
| ENSMUSG00000091971 | Hspa1a | ENSMUSG00000001918 | Slc1a5 |
| ENSMUSG00000028654 | Mycl | ENSMUSG00000053228 | Ceacam3 |
| ENSMUSG00000031951 | Tmem231 | ENSMUSG00000040987 | Mill2 |
| ENSMUSG00000039452 | Snx22 | ENSMUSG00000002983 | Relb |
| ENSMUSG00000060509 | Xcr1 | ENSMUSG00000062300 | Nectin2 |
| ENSMUSG00000031355 | Arhgap6 | ENSMUSG00000040525 | Cblc |
| ENSMUSG00000025938 | Slco5a1 | ENSMUSG00000040511 | Pvr |
| ENSMUSG00000025964 | Adam23 | ENSMUSG00000003379 | Cd79a |
| ENSMUSG00000039395 | Mreg | ENSMUSG00000002602 | Axl |
| ENSMUSG00000005338 | Cadm3 | ENSMUSG00000030603 | Psmc4 |
| ENSMUSG00000020926 | Adam11 | ENSMUSG00000002068 | Ccne1 |
| ENSMUSG00000021087 | Rtn1 | ENSMUSG00000039013 | Siglecf |
| ENSMUSG00000004562 | Arhgef40 | ENSMUSG00000004612 | Nkg7 |
| ENSMUSG00000044309 | Apol7c | ENSMUSG00000008193 | Spib |
| ENSMUSG00000003352 | Cacnb3 | ENSMUSG00000038644 | Pold1 |
| ENSMUSG00000075269 | Bex6 | ENSMUSG00000003184 | Irf3 |
| ENSMUSG00000024124 | Prss30 | ENSMUSG00000003873 | Bax |
| ENSMUSG00000015468 | Notch4 | ENSMUSG00000063229 | Ldha |
| ENSMUSG00000028327 | Stra6l | ENSMUSG00000030605 | Mfge8 |
| ENSMUSG00000029101 | Rgs12 | ENSMUSG00000030528 | Blm |
| ENSMUSG00000029581 | Fscn1 | ENSMUSG00000001741 | Il16 |
| ENSMUSG00000031486 | Adgra2 | ENSMUSG00000015709 | Arnt2 |
| ENSMUSG00000005947 | Itgae | ENSMUSG00000015957 | Wnt11 |
| ENSMUSG00000025779 | Ly96 | ENSMUSG00000070436 | Serpinh1 |
| ENSMUSG00000026155 | Smap1 | ENSMUSG00000070427 | Il18bp |
| ENSMUSG00000026117 | Zap70 | ENSMUSG00000030966 | Trim21 |
| ENSMUSG00000026073 | Il1r2 | ENSMUSG00000030790 | Adm |
| ENSMUSG00000062939 | Stat4 | ENSMUSG00000034990 | Otoa |
| ENSMUSG00000026104 | Stat1 | ENSMUSG00000030695 | Aldoa |
| ENSMUSG00000026103 | Gls | ENSMUSG00000042492 | Tbc1d10b |
| ENSMUSG00000026029 | Casp8 | ENSMUSG00000030830 | Itgal |
| ENSMUSG00000026012 | Cd28 | ENSMUSG00000030789 | Itgax |
| ENSMUSG00000026009 | Icos | ENSMUSG00000054555 | Adam12 |
| ENSMUSG00000026180 | Cxcr2 | ENSMUSG00000031004 | Mki67 |
| ENSMUSG00000026177 | Slc11a1 | ENSMUSG00000054612 | Mgmt |
| ENSMUSG00000026167 | Wnt10a | ENSMUSG00000078566 | Bnip3 |
| ENSMUSG00000006538 | Ihh | ENSMUSG00000060591 | Ifitm2 |
| ENSMUSG00000026213 | Stk11ip | ENSMUSG00000025491 | Ifitm1 |
| ENSMUSG00000043230 | Fam124b | ENSMUSG00000054065 | Pkp3 |
| ENSMUSG00000026166 | Ccl20 | ENSMUSG00000025499 | Hras |
| ENSMUSG00000048126 | Col6a3 | ENSMUSG00000025498 | Irf7 |
| ENSMUSG00000007805 | Twist2 | ENSMUSG00000037664 | Cdkn1c |
| ENSMUSG00000026313 | Hdac4 | ENSMUSG00000031077 | Fadd |
| ENSMUSG00000026285 | Pdcd1 | ENSMUSG00000070348 | Ccnd1 |
| ENSMUSG00000067006 | Serpinb5 | ENSMUSG00000040197 | Cd209e |
| ENSMUSG00000026390 | Marco | ENSMUSG00000023235 | Ccl25 |
| ENSMUSG00000045382 | Cxcr4 | ENSMUSG00000031465 | Angpt2 |
| ENSMUSG00000026420 | Il24 | ENSMUSG00000031537 | Ikbkb |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000016529 | Il10 | ENSMUSG00000031548 | Sfrp1 |
| ENSMUSG00000070645 | Ren1 | ENSMUSG00000031551 | Ido1 |
| ENSMUSG00000026429 | Ube2t | ENSMUSG00000031565 | Fgfr1 |
| ENSMUSG00000026395 | Ptprc | ENSMUSG00000031490 | Eif4ebp1 |
| ENSMUSG00000032487 | Ptgs2 | ENSMUSG00000031529 | Tnks |
| ENSMUSG00000026479 | Lamc2 | ENSMUSG00000031639 | Tlr3 |
| ENSMUSG00000026700 | Tnfsf4 | ENSMUSG00000031628 | Casp3 |
| ENSMUSG00000066755 | Tnfsf18 | ENSMUSG00000031627 | Irf2 |
| ENSMUSG00000000817 | Fasl | ENSMUSG00000031520 | Vegfc |
| ENSMUSG00000026582 | Sele | ENSMUSG00000036246 | Gmip |
| ENSMUSG00000026580 | Selp | ENSMUSG00000031849 | Comp |
| ENSMUSG00000038463 | Olfml2b | ENSMUSG00000056204 | Pgpep1 |
| ENSMUSG00000070524 | Fcrlb | ENSMUSG00000031834 | Pik3r2 |
| ENSMUSG00000026656 | Fcgr2b | ENSMUSG00000031805 | Jak3 |
| ENSMUSG00000059089 | Fcgr4 | ENSMUSG00000031712 | Il15 |
| ENSMUSG00000004709 | Cd244a | ENSMUSG00000055994 | Nod2 |
| ENSMUSG00000004707 | Ly9 | ENSMUSG00000056608 | Chd9 |
| ENSMUSG00000015355 | Cd48 | ENSMUSG00000031666 | Rbl2 |
| ENSMUSG00000038147 | Cd84 | ENSMUSG00000074151 | Nlrc5 |
| ENSMUSG00000005339 | Fcer1a | ENSMUSG00000031779 | Ccl22 |
| ENSMUSG00000039997 | Ifi203 | ENSMUSG00000031778 | Cx3cl1 |
| ENSMUSG00000039748 | Exo1 | ENSMUSG00000031780 | Ccl17 |
| ENSMUSG00000079164 | Tlr5 | ENSMUSG00000031672 | Got2 |
| ENSMUSG00000039239 | Tgfb2 | ENSMUSG00000031673 | Cdh11 |
| ENSMUSG00000026605 | Cenpf | ENSMUSG00000031871 | Cdh5 |
| ENSMUSG00000026630 | Batf3 | ENSMUSG00000096188 | Cmtm4 |
| ENSMUSG00000026628 | Atf3 | ENSMUSG00000069922 | Ces3a |
| ENSMUSG00000026639 | Lamb3 | ENSMUSG00000031897 | Psmb10 |
| ENSMUSG00000016194 | Hsd11b1 | ENSMUSG00000000303 | Cdh1 |
| ENSMUSG00000019768 | Esr1 | ENSMUSG00000040010 | Slc7a5 |
| ENSMUSG00000046916 | Myct1 | ENSMUSG00000032815 | Fanca |
| ENSMUSG00000079685 | Ulbp1 | ENSMUSG00000025888 | Casp1 |
| ENSMUSG00000019850 | Tnfaip3 | ENSMUSG00000050578 | Mmp13 |
| ENSMUSG00000071369 | Map3k5 | ENSMUSG00000049723 | Mmp12 |
| ENSMUSG00000019970 | Sgk1 | ENSMUSG00000043089 | Mmp1a |
| ENSMUSG00000019987 | Arg1 | ENSMUSG00000018623 | Mmp7 |
| ENSMUSG00000019843 | Fyn | ENSMUSG00000032000 | Birc3 |
| ENSMUSG00000019916 | P4ha1 | ENSMUSG00000031925 | Maml2 |
| ENSMUSG00000020101 | Vsir | ENSMUSG00000049307 | Fut4 |
| ENSMUSG00000037012 | Hk1 | ENSMUSG00000031928 | Mre11a |
| ENSMUSG00000020178 | Adora2a | ENSMUSG00000004099 | Dnmt1 |
| ENSMUSG00000000290 | Itgb2 | ENSMUSG00000037405 | Icam1 |
| ENSMUSG00000000732 | Icosl | ENSMUSG00000032174 | Icam5 |
| ENSMUSG00000020312 | Shc2 | ENSMUSG00000036777 | Anln |
| ENSMUSG00000020325 | Fstl3 | ENSMUSG00000032125 | Robo4 |
| ENSMUSG00000035673 | Sbno2 | ENSMUSG00000047880 | Cxcr5 |
| ENSMUSG00000020167 | Tcf3 | ENSMUSG00000032089 | Il10ra |
| ENSMUSG00000035242 | Oaz1 | ENSMUSG00000039542 | Ncam1 |
| ENSMUSG00000004934 | Pias4 | ENSMUSG00000039217 | Il18 |
| ENSMUSG00000069515 | Lyz1 | ENSMUSG00000034218 | Atm |
| ENSMUSG00000020184 | Mdm2 | ENSMUSG00000032298 | Neil1 |
| ENSMUSG00000025407 | Gli1 | ENSMUSG00000035914 | Cd276 |
| ENSMUSG00000040280 | Ndufa4l2 | ENSMUSG00000032375 | Aph1b |
| ENSMUSG00000040033 | Stat2 | ENSMUSG00000032366 | Tpm1 |
| ENSMUSG00000025358 | Cdk2 | ENSMUSG00000032204 | Aqp9 |
| ENSMUSG00000025354 | Dnajc14 | ENSMUSG00000032344 | Cgas |
| ENSMUSG00000002129 | Sf3a1 | ENSMUSG00000032420 | Nt5e |
| ENSMUSG00000034394 | Lif | ENSMUSG00000032356 | Rasgrf1 |
| ENSMUSG00000018654 | Ikzf1 | ENSMUSG00000032374 | Plod2 |
| ENSMUSG00000020122 | Egfr | ENSMUSG00000045322 | Tlr9 |
| ENSMUSG00000057967 | Fgf18 | ENSMUSG00000032596 | Uba7 |
| ENSMUSG00000020399 | Havcr2 | ENSMUSG00000032498 | Mlh1 |
| ENSMUSG00000020380 | Rad50 | ENSMUSG00000046785 | Epm2aip1 |
| ENSMUSG00000018899 | Irf1 | ENSMUSG00000047898 | Ccr4 |
| ENSMUSG00000018906 | P4ha2 | ENSMUSG00000032434 | Cmtm6 |
| ENSMUSG00000018916 | Csf2 | ENSMUSG00000032440 | Tgfbr2 |
| ENSMUSG00000009900 | Wnt3a | ENSMUSG00000032508 | Myd88 |
| ENSMUSG00000032691 | Nlrp3 | ENSMUSG00000006932 | Ctnnb1 |
| ENSMUSG00000020538 | Srebf1 | ENSMUSG00000029530 | Ccr9 |
| ENSMUSG00000019505 | Ubb | ENSMUSG00000049103 | Ccr2 |
| ENSMUSG00000020901 | Pik3r5 | ENSMUSG00000079227 | Ccr5 |
| ENSMUSG00000059552 | Trp53 | ENSMUSG00000015340 | Cybb |
| ENSMUSG00000018774 | Cd68 | ENSMUSG00000037358 | Dipk2b |
| ENSMUSG00000089669 | Tnfsf13 | ENSMUSG00000005696 | Sh2d1a |
| ENSMUSG00000097328 | Tnfsf12 | ENSMUSG00000031119 | Gpc4 |
| ENSMUSG00000005198 | Polr2a | ENSMUSG00000031132 | Cd40lg |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000000317 | Bcl6b | ENSMUSG00000031137 | Fgf13 |
| ENSMUSG00000018920 | Cxcl16 | ENSMUSG00000033343 | Magea4 |
| ENSMUSG00000017390 | Aldoc | ENSMUSG00000004221 | Ikbkg |
| ENSMUSG00000020826 | Nos2 | ENSMUSG00000031400 | G6pdx |
| ENSMUSG00000020716 | Nf1 | ENSMUSG00000035725 | Prkx |
| ENSMUSG00000020676 | Ccl11 | ENSMUSG00000035427 | Mageb4 |
| ENSMUSG00000009185 | Ccl8 | ENSMUSG00000031304 | Il2rg |
| ENSMUSG00000020702 | Ccl1 | ENSMUSG00000057439 | Kir3dl2 |
| ENSMUSG00000035042 | Ccl5 | ENSMUSG00000031424 | Kir3dl1 |
| ENSMUSG00000019122 | Ccl9 | ENSMUSG00000031274 | Col4a5 |
| ENSMUSG00000018927 | Ccl6 | ENSMUSG00000094196 | Magea3 |
| ENSMUSG00000000982 | Ccl3 | ENSMUSG00000096644 | Magea1 |
| ENSMUSG00000018930 | Ccl4 | ENSMUSG00000040522 | Tlr8 |
| ENSMUSG00000034329 | Brip1 | ENSMUSG00000026573 | Xcl1 |
| ENSMUSG00000020516 | Rps6kb1 | ENSMUSG00000020027 | Socs2 |
| ENSMUSG00000007646 | Rad51c | ENSMUSG00000050222 | Il17d |
| ENSMUSG00000000120 | Ngfr | ENSMUSG00000022015 | Tnfsf11 |
| ENSMUSG00000071415 | Rpl23 | ENSMUSG00000000489 | Pdgfb |
| ENSMUSG00000062312 | Erbb2 | ENSMUSG00000039481 | Nrtn |
| ENSMUSG00000018168 | Ikzf3 | ENSMUSG00000002603 | Tgfb1 |
| ENSMUSG00000038067 | Csf3 | ENSMUSG00000045826 | Ptprcap |
| ENSMUSG00000001552 | Jup | ENSMUSG00000076431 | Sox4 |
| ENSMUSG00000004040 | Stat3 | ENSMUSG00000029705 | Cux1 |
| ENSMUSG00000010358 | Ifi35 | ENSMUSG00000008496 | Pou2f2 |
| ENSMUSG00000017146 | Brca1 | ENSMUSG00000041515 | Irf8 |
| ENSMUSG00000008855 | Hdac5 | ENSMUSG00000026189 | Peer |
| ENSMUSG00000034757 | Tmub2 | ENSMUSG00000056220 | Pla2g4a |
| ENSMUSG00000020689 | Itgb3 | ENSMUSG00000026473 | Glul |
| ENSMUSG00000020694 | Tlk2 | ENSMUSG00000026471 | Mr1 |
| ENSMUSG00000001029 | Icam2 | ENSMUSG00000019818 | Cd164 |
| ENSMUSG00000020717 | Pecam1 | ENSMUSG00000020432 | Tcn2 |
| ENSMUSG00000050965 | Prkca | ENSMUSG00000020604 | Arsg |
| ENSMUSG00000034652 | Cd300a | ENSMUSG00000050103 | Agmo |
| ENSMUSG00000017716 | Birc5 | ENSMUSG00000035711 | Dok3 |
| ENSMUSG00000025583 | Rptor | ENSMUSG00000021477 | Ctsl |
| ENSMUSG00000025163 | Cd7 | ENSMUSG00000021710 | Nln |
| ENSMUSG00000020649 | Rrm2 | ENSMUSG00000041707 | Tmem273 |
| ENSMUSG00000020641 | Rsad2 | ENSMUSG00000037824 | Tspan14 |
| ENSMUSG00000063632 | Sox11 | ENSMUSG00000064373 | Selenop |
| ENSMUSG00000020573 | Pik3cg | ENSMUSG00000081534 | Slc48a1 |
| ENSMUSG00000035799 | Twist1 | ENSMUSG00000022788 | Fgd4 |
| ENSMUSG00000073079 | Srp54a | ENSMUSG00000000326 | Comt |
| ENSMUSG00000021025 | Nfkbia | ENSMUSG00000000127 | Fer |
| ENSMUSG00000045930 | Clec14a | ENSMUSG00000005803 | Sqor |
| ENSMUSG00000021109 | Hif1a | ENSMUSG00000014361 | Mertk |
| ENSMUSG00000021125 | Arg2 | ENSMUSG00000027900 | Dram2 |
| ENSMUSG00000021253 | Tgfb3 | ENSMUSG00000039005 | Tlr4 |
| ENSMUSG00000021179 | Nrde2 | ENSMUSG00000028497 | Hacd4 |
| ENSMUSG00000057963 | Itpk1 | ENSMUSG00000028859 | Csf3r |
| ENSMUSG00000064215 | Ifi27 | ENSMUSG00000019055 | Plod1 |
| ENSMUSG00000066366 | Serpina1a | ENSMUSG00000029759 | Pon3 |
| ENSMUSG00000041359 | Tcl1 | ENSMUSG00000061758 | Akrlb10 |
| ENSMUSG00000001729 | Akt1 | ENSMUSG00000029925 | Tbxas1 |
| ENSMUSG00000002799 | Jag2 | ENSMUSG00000029998 | Pcyox1 |
| ENSMUSG00000025321 | Itgb8 | ENSMUSG00000030272 | Camk1 |
| ENSMUSG00000021303 | Gng4 | ENSMUSG00000040466 | Blvrb |
| ENSMUSG00000021319 | Sfrp4 | ENSMUSG00000003363 | Pld3 |
| ENSMUSG00000016477 | E2f3 | ENSMUSG00000030761 | Myo7a |
| ENSMUSG00000021408 | Ripk1 | ENSMUSG00000030894 | Tpp1 |
| ENSMUSG00000021367 | Edn1 | ENSMUSG00000007891 | Ctsd |
| ENSMUSG00000021379 | Id4 | ENSMUSG00000042870 | Tom1 |
| ENSMUSG00000021457 | Syk | ENSMUSG00000031903 | Pla2g15 |
| ENSMUSG00000021464 | Ror2 | ENSMUSG00000016534 | Lamp2 |
| ENSMUSG00000021474 | Sfxn1 | ENSMUSG00000044583 | Tlr7 |
| ENSMUSG00000021508 | Cxcl14 | ENSMUSG00000059498 | Fcgr3 |
| ENSMUSG00000021540 | Smad5 | ENSMUSG00000051439 | Cd14 |
| ENSMUSG00000052957 | Gas1 | ENSMUSG00000026131 | Dst |
| ENSMUSG00000069805 | Fbp1 | ENSMUSG00000047793 | Sned1 |
| ENSMUSG00000021577 | Sdha | ENSMUSG00000019944 | Rhobtb1 |
| ENSMUSG00000021614 | Vcan | ENSMUSG00000034714 | Ttyh2 |
| ENSMUSG00000021678 | F2rl1 | ENSMUSG00000022272 | Myo10 |
| ENSMUSG00000021650 | Ptcd2 | ENSMUSG00000052942 | Glis3 |
| ENSMUSG00000041431 | Ccnb1 | ENSMUSG00000028184 | Adgrl2 |
| ENSMUSG00000041417 | Pik3r1 | ENSMUSG00000034853 | Acot11 |
| ENSMUSG00000042417 | Ccno | ENSMUSG00000042476 | Abcb4 |
| ENSMUSG00000042284 | Itga1 | ENSMUSG00000023079 | Gtf2ird1 |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000074715 | Ccl28 | ENSMUSG00000030064 | Frmd4b |
| ENSMUSG00000025278 | Flnb | ENSMUSG00000030409 | Dmpk |
| ENSMUSG00000021806 | Nid2 | ENSMUSG00000034656 | Cacna1a |
| ENSMUSG00000021994 | Wnt5a | ENSMUSG00000032014 | Oaf |
| ENSMUSG00000021794 | Glud1 | ENSMUSG00000006014 | Prg4 |
| ENSMUSG00000041445 | Mmrn2 | ENSMUSG00000069919 | Hba-a1 |
| ENSMUSG00000021831 | Ero1l | ENSMUSG00000069917 | Hba-a2 |
| ENSMUSG00000022193 | Psmb5 | ENSMUSG00000020773 | Trim47 |
| ENSMUSG00000040618 | Pck2 | ENSMUSG00000006356 | Crip2 |
| ENSMUSG00000002325 | Irf9 | ENSMUSG00000095079 | Igha |
| ENSMUSG00000022221 | Ripk3 | ENSMUSG00000076612 | Ighg2c |
| ENSMUSG00000022156 | Gzme | ENSMUSG00000076613 | Ighg2b |
| ENSMUSG00000054509 | Parp4 | ENSMUSG00000023031 | Cela1 |
| ENSMUSG00000021974 | Fgf9 | ENSMUSG00000083282 | Ctsf |
| ENSMUSG00000014453 | Blk | ENSMUSG00000060224 | Pyroxd2 |
| ENSMUSG00000045731 | Pnoc | ENSMUSG00000032890 | Rims3 |
| ENSMUSG00000022051 | Bnip3l | ENSMUSG00000067149 | Jchain |
| ENSMUSG00000014813 | Stc1 | ENSMUSG00000076569 | Igkv5-39 |
| ENSMUSG00000034205 | Loxl2 | ENSMUSG00000030084 | Plxna1 |
| ENSMUSG00000022105 | Rb1 | ENSMUSG00000073940 | Hbb-bt |
| ENSMUSG00000055737 | Ghr | ENSMUSG00000052305 | Hbb-bs |
| ENSMUSG00000079105 | C7 | ENSMUSG00000025511 | Tspan4 |
| ENSMUSG00000039942 | Ptger4 | ENSMUSG00000025151 | Maged1 |
| ENSMUSG00000022150 | Dab2 | ENSMUSG00000005087 | Cd44 |
| ENSMUSG00000050310 | Rictor | ENSMUSG00000046841 | Ckap4 |
| ENSMUSG00000005268 | Prlr | ENSMUSG00000044986 | Tst |
| ENSMUSG00000022309 | Angpt1 | ENSMUSG00000024659 | Anxa1 |
| ENSMUSG00000063727 | Tnfrsf11b | ENSMUSG00000074570 | Cass4 |
| ENSMUSG00000022419 | Deptor | ENSMUSG00000074340 | Ovgp1 |
| ENSMUSG00000079018 | Ly6c1 | ENSMUSG00000106671 | Gm42900 |
| ENSMUSG00000033576 | Apol6 | ENSMUSG00000056091 | St3gal5 |
| ENSMUSG00000071713 | Csf2rb | ENSMUSG00000030413 | Pglyrp1 |
| ENSMUSG00000068227 | H2rb | ENSMUSG00000009628 | Tex15 |
| ENSMUSG00000018169 | Mfng | ENSMUSG00000009633 | G0s2 |
| ENSMUSG00000033006 | Sox10 | ENSMUSG00000000204 | Slfn4 |
| ENSMUSG00000058099 | Nfam1 | ENSMUSG00000025161 | Slc16a3 |
| ENSMUSG00000036106 | Prr5 | ENSMUSG00000021360 | Gcnt2 |
| ENSMUSG00000022382 | Wnt7b | ENSMUSG00000022564 | Grina |
| ENSMUSG00000022615 | Tymp | ENSMUSG00000001227 | Sema6b |
| ENSMUSG00000022451 | Twf1 | ENSMUSG00000058624 | Gda |
| ENSMUSG00000033065 | Pfkm | ENSMUSG00000086564 | Cd101 |
| ENSMUSG00000023050 | Map3k12 | ENSMUSG00000051397 | Tacstd2 |
| ENSMUSG00000039457 | Ppl | ENSMUSG00000033720 | Sfxn5 |
| ENSMUSG00000038037 | Socs1 | ENSMUSG00000030340 | Scnn1a |
| ENSMUSG00000022496 | Tnfrsf17 | ENSMUSG00000004609 | Cd33 |
| ENSMUSG00000049502 | Dtx3l | ENSMUSG00000041268 | Dmxl2 |
| ENSMUSG00000022906 | Parp9 | ENSMUSG00000073489 | Ifi204 |
| ENSMUSG00000022901 | Cd86 | ENSMUSG00000038188 | Scarf1 |
| ENSMUSG00000002847 | Pla1a | ENSMUSG00000017417 | Plxdc1 |
| ENSMUSG00000075122 | Cd80 | ENSMUSG00000079017 | Ifi27l2a |
| ENSMUSG00000071552 | Tigit | ENSMUSG00000006360 | Crip1 |
| ENSMUSG00000022667 | Cd200r1 | ENSMUSG00000076614 | Ighg1 |
| ENSMUSG00000022657 | Cd96 | ENSMUSG00000022587 | Ly6e |
| ENSMUSG00000055447 | Cd47 | ENSMUSG00000024675 | Ms4a4c |
| ENSMUSG00000022876 | Samsn1 | ENSMUSG00000041488 | Stx3 |
| ENSMUSG00000022967 | Ifnar1 | ENSMUSG00000035273 | Hpse |
| ENSMUSG00000000386 | Mx1 | ENSMUSG00000038387 | Rras |
| ENSMUSG00000023830 | Igf2r | ENSMUSG00000026193 | Fn1 |
| ENSMUSG00000014773 | Dll1 | ENSMUSG00000026365 | Cfh |
| ENSMUSG00000014767 | Tbp | ENSMUSG00000026536 | Ifi211 |
| ENSMUSG00000045551 | Fpr1 | ENSMUSG00000039109 | F13a1 |
| ENSMUSG00000079700 | Fpr3 | ENSMUSG00000022584 | Ly6c2 |
| ENSMUSG00000055839 | Elob | ENSMUSG00000079419 | Ms4a6c |
| ENSMUSG00000024173 | Tpsab1 | ENSMUSG00000024679 | Ms4a6d |
| ENSMUSG00000024182 | Axin1 | ENSMUSG00000026796 | Fam129b |
| ENSMUSG00000046711 | Hmga1 | ENSMUSG00000048058 | Ldlrad3 |
| ENSMUSG00000023067 | Cdkn1a | ENSMUSG00000027435 | Cd93 |
| ENSMUSG00000024002 | Brd4 | ENSMUSG00000027994 | Mcub |
| ENSMUSG00000002289 | Angptl4 | ENSMUSG00000034557 | Zfyve9 |
| ENSMUSG00000024308 | Tapbp | ENSMUSG00000040964 | Arhgef10l |
| ENSMUSG00000061232 | H2-K1 | ENSMUSG00000029322 | Plac8 |
| ENSMUSG00000024330 | Col11a2 | ENSMUSG00000038156 | Spon1 |
| ENSMUSG00000098241 | H2-Pa | ENSMUSG00000031444 | F10 |
| ENSMUSG00000037649 | H2-DMa | ENSMUSG00000014846 | Tppp3 |
| ENSMUSG00000096727 | Psmb9 | ENSMUSG00000047409 | Ctdspl |
| ENSMUSG00000037321 | Tap1 | ENSMUSG00000030786 | Itgam |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000024338 | Psmb8 | ENSMUSG00000022074 | Tnfrsf10b |
| ENSMUSG00000024339 | Tap2 | ENSMUSG00000022965 | Ifngr2 |
| ENSMUSG00000041538 | H2-Ob | ENSMUSG00000002897 | Il17ra |
| ENSMUSG00000034786 | Gpsm3 | ENSMUSG00000030341 | Tnfrsf1a |
| ENSMUSG00000024371 | C2 | ENSMUSG00000030745 | Il21r |
| ENSMUSG00000024399 | Ltb | ENSMUSG00000004043 | Stat5a |
| ENSMUSG00000073411 | H2-D1 | ENSMUSG00000009739 | Pou6f1 |
| ENSMUSG00000079507 | H2-Q1 | ENSMUSG00000022521 | Crebbp |
| ENSMUSG00000091705 | H2-Q2 | ENSMUSG00000030067 | Foxp1 |
| ENSMUSG00000067235 | H2-Q10 | ENSMUSG00000022582 | Ly6g |
| ENSMUSG00000038762 | Abcf1 | ENSMUSG00000015533 | Itga2 |
| ENSMUSG00000067212 | H2-T23 | ENSMUSG00000067750 | Khdc1a |
| ENSMUSG00000016206 | H2-M3 | ENSMUSG00000037202 | Prf1 |
| ENSMUSG00000023947 | Nfkbie | ENSMUSG00000023132 | Gzma |
| ENSMUSG00000023951 | Vegfa | ENSMUSG00000030114 | Klrg1 |
| ENSMUSG00000034165 | Ccnd3 | ENSMUSG00000030361 | Klrb1a |
| ENSMUSG00000042265 | Trem1 | ENSMUSG00000030325 | Klrb1c |
| ENSMUSG00000023992 | Trem2 | ENSMUSG00000079298 | Klrb1b |
| ENSMUSG00000000708 | Kat2b | ENSMUSG00000050241 | Klre1 |
| ENSMUSG00000047123 | Ticam1 | ENSMUSG00000030149 | Klrk1 |
| ENSMUSG00000035678 | Tnfsf9 | ENSMUSG00000062524 | Ncr1 |
| ENSMUSG00000019489 | Cd70 | ENSMUSG00000045087 | S1pr5 |
| ENSMUSG00000004730 | Adgre1 | ENSMUSG00000032446 | Eomes |
| ENSMUSG00000032796 | Lama1 | ENSMUSG00000026121 | Sema4c |
| ENSMUSG00000024079 | Eif2ak2 | ENSMUSG00000104117 | Gm20743 |
| ENSMUSG00000045394 | Epcam | ENSMUSG00000045827 | Serpinb9 |
| ENSMUSG00000024151 | Msh2 | ENSMUSG00000104876 | Trdc |
| ENSMUSG00000005370 | Msh6 | ENSMUSG00000078202 | Nrarp |
| ENSMUSG00000024232 | Bambi | ENSMUSG00000043102 | Qrfp |
| ENSMUSG00000024235 | Map3k8 | ENSMUSG00000028214 | Gem |
| ENSMUSG00000024238 | Zeb1 | ENSMUSG00000032135 | Mcam |
| ENSMUSG00000036904 | Fzd8 | ENSMUSG00000059901 | Adamts14 |
| ENSMUSG00000024290 | Rock1 | ENSMUSG00000022114 | Spry2 |
| ENSMUSG00000024304 | Cdh2 | ENSMUSG00000043932 | Klri2 |
| ENSMUSG00000059898 | Dsc3 | ENSMUSG00000079852 | Klra4 |
| ENSMUSG00000024382 | Ercc3 | ENSMUSG00000089727 | Klra8 |
| ENSMUSG00000024379 | Tslp | ENSMUSG00000033024 | Klra9 |
| ENSMUSG00000005871 | Apc | ENSMUSG00000067591 | Klra3 |
| ENSMUSG00000044201 | Cdc25c | ENSMUSG00000032899 | Styki |
| ENSMUSG00000038418 | Egr1 | ENSMUSG00000020900 | Myh10 |
| ENSMUSG00000051486 | Pcdhb11 | ENSMUSG00000075033 | Nxpe3 |
| ENSMUSG00000024454 | Hdac3 | ENSMUSG00000023805 | Synj2 |
| ENSMUSG00000024427 | Spry4 | ENSMUSG00000026950 | Neb |
| ENSMUSG00000024620 | Pdgfrb | ENSMUSG00000027546 | Atp9a |
| ENSMUSG00000024621 | Csf1r | ENSMUSG00000085028 | Slc2a4rg-ps |
| ENSMUSG00000033871 | Ppargc1b | ENSMUSG00000051444 | Bbs12 |
| ENSMUSG00000024892 | Pcx | ENSMUSG00000091575 | 2010016I18Rik |
| ENSMUSG00000006464 | Bbs1 | ENSMUSG00000030319 | Cand2 |
| ENSMUSG00000024912 | Fosl1 | ENSMUSG00000055675 | Kbtbd11 |
| ENSMUSG00000024910 | Ctsw | ENSMUSG00000032221 | Mns1 |
| ENSMUSG00000024927 | Rela | ENSMUSG00000056418 | BC043934 |
| ENSMUSG00000024959 | Bad | ENSMUSG00000070942 | Il1rl2 |
| ENSMUSG00000024962 | Vegfb | ENSMUSG00000009350 | Mpo |
| ENSMUSG00000024669 | Cd5 | ENSMUSG00000017493 | Igfbp4 |
| ENSMUSG00000101389 | Ms4a4a | ENSMUSG00000004558 | Ndrg2 |
| ENSMUSG00000024677 | Ms4a6b | ENSMUSG00000028644 | Ermap |
| ENSMUSG00000024680 | Ms4a2 | ENSMUSG00000028943 | Espn |
| ENSMUSG00000039982 | Dtx4 | ENSMUSG00000029359 | Tesc |
| ENSMUSG00000016496 | Cd274 | ENSMUSG00000086894 | Gm15708 |
| ENSMUSG00000016498 | Pdcd1lg2 | ENSMUSG00000029869 | Ephb6 |
| ENSMUSG00000024806 | Mlana | ENSMUSG00000090958 | Lrrc32 |
| ENSMUSG00000024810 | Il33 | ENSMUSG00000035239 | Neu3 |
| ENSMUSG00000024868 | Dkk1 | ENSMUSG00000045659 | Plekha7 |
| ENSMUSG00000013663 | Pten | ENSMUSG00000012889 | Podnl1 |
| ENSMUSG00000071573 | Rnls | ENSMUSG00000031933 | Izumo1r |
| ENSMUSG00000024778 | Fas | ENSMUSG00000039384 | Dusp10 |
| ENSMUSG00000045932 | Ifit2 | ENSMUSG00000021699 | Pde4d |
| ENSMUSG00000074896 | Ifit3 | ENSMUSG00000033022 | Cdo1 |
| ENSMUSG00000034459 | Ifit1 | ENSMUSG00000047604 | Frat2 |
| ENSMUSG00000024989 | Cep55 | ENSMUSG00000100826 | Snhg14 |
| ENSMUSG00000025001 | Hells | ENSMUSG00000050382 | Kif7 |
| ENSMUSG00000048120 | Entpd1 | ENSMUSG00000069920 | B3gnt9 |
| ENSMUSG00000025190 | Got1 | ENSMUSG00000035202 | Lars2 |
| ENSMUSG00000025199 | Chuk | ENSMUSG00000002006 | Pdzd4 |
| ENSMUSG00000025225 | Nfkb2 | ENSMUSG00000041757 | Plekha6 |
| ENSMUSG00000025064 | Col17a1 | ENSMUSG00000025359 | Pmel |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000025025 | Mxi1 | ENSMUSG00000051166 | Eml5 |
| ENSMUSG00000034765 | Dusp5 | ENSMUSG00000057132 | Rpgrip1 |
| ENSMUSG00000025782 | Taf3 | ENSMUSG00000035235 | Trim13 |
| ENSMUSG00000026773 | Pfkfb3 | ENSMUSG00000052005 | Gm9864 |
| ENSMUSG00000026712 | Mrc1 | ENSMUSG00000060227 | Casc4 |
| ENSMUSG00000026981 | Il1rn | ENSMUSG00000089417 | Gm22009 |
| ENSMUSG00000026923 | Notch1 | ENSMUSG00000033295 | Ptprf |
| ENSMUSG00000062647 | Rpl7a | ENSMUSG00000105742 | Gm42748 |
| ENSMUSG00000026918 | Brd3 | ENSMUSG00000064023 | Klk8 |
| ENSMUSG00000026837 | Col5a1 | ENSMUSG00000051504 | Siglech |
| ENSMUSG00000026835 | Fcnb | ENSMUSG00000025104 | Hdgfl3 |
| ENSMUSG00000026874 | He | ENSMUSG00000001986 | Gria3 |
| ENSMUSG00000053475 | Tnfaip6 | ENSMUSG00000005763 | Cd247 |
| ENSMUSG00000026834 | Acvr1c | ENSMUSG00000026770 | Il2ra |
| ENSMUSG00000000392 | Fap | ENSMUSG00000002033 | Cd3g |
| ENSMUSG00000026896 | Ifih1 | ENSMUSG00000032094 | Cd3d |
| ENSMUSG00000027111 | Itga6 | ENSMUSG00000032093 | Cd3e |
| ENSMUSG00000006494 | Pdk1 | ENSMUSG00000026358 | Rgs1 |
| ENSMUSG00000075271 | Ttc30a1 | ENSMUSG00000042684 | Npl |
| ENSMUSG00000027009 | Itga4 | ENSMUSG00000020377 | Ltc4s |
| ENSMUSG00000027087 | Itgav | ENSMUSG00000001123 | Lgals9 |
| ENSMUSG00000044338 | Aplnr | ENSMUSG00000035385 | Ccl2 |
| ENSMUSG00000002109 | Ddb2 | ENSMUSG00000035373 | Ccl7 |
| ENSMUSG00000027193 | Apis | ENSMUSG00000035352 | Ccl12 |
| ENSMUSG00000040152 | Thbs1 | ENSMUSG00000021665 | Hexb |
| ENSMUSG00000027323 | Rad51 | ENSMUSG00000022912 | Pros1 |
| ENSMUSG00000027314 | Dll4 | ENSMUSG00000024190 | Dusp1 |
| ENSMUSG00000027242 | Wdr76 | ENSMUSG00000003541 | Ier3 |
| ENSMUSG00000060802 | B2m | ENSMUSG00000024672 | Ms4a7 |
| ENSMUSG00000027360 | Hdc | ENSMUSG00000027293 | Ehd4 |
| ENSMUSG00000027368 | Dusp2 | ENSMUSG00000027199 | Gatm |
| ENSMUSG00000027399 | Il1a | ENSMUSG00000015852 | Fcrls |
| ENSMUSG00000027398 | Il1b | ENSMUSG00000015947 | Fcgr1 |
| ENSMUSG00000037902 | Sirpa | ENSMUSG00000028195 | Ccn1 |
| ENSMUSG00000027322 | Siglec1 | ENSMUSG00000015243 | Abca1 |
| ENSMUSG00000027358 | Bmp2 | ENSMUSG00000028494 | Plin2 |
| ENSMUSG00000027276 | Jag1 | ENSMUSG00000029484 | Anxa3 |
| ENSMUSG00000074743 | Thbd | ENSMUSG00000029304 | Spp1 |
| ENSMUSG00000007659 | Bcl2l1 | ENSMUSG00000040552 | C3ar1 |
| ENSMUSG00000003283 | Hck | ENSMUSG00000002985 | Apoe |
| ENSMUSG00000001403 | Ube2c | ENSMUSG00000048779 | P2ry6 |
| ENSMUSG00000017737 | Mmp9 | ENSMUSG00000031451 | Gas6 |
| ENSMUSG00000017652 | Cd40 | ENSMUSG00000031659 | Adcy7 |
| ENSMUSG00000042821 | Snai1 | ENSMUSG00000043953 | Ccrl2 |
| ENSMUSG00000056501 | Cebpb | ENSMUSG00000025804 | Ccr1 |
| ENSMUSG00000027544 | Nfatc2 | ENSMUSG00000025283 | Sat1 |
| ENSMUSG00000040289 | Hey1 | ENSMUSG00000055170 | Ifng |
| ENSMUSG00000078780 | Gm5150 | ENSMUSG00000014599 | Csf1 |
| ENSMUSG00000001865 | Cpa3 | ENSMUSG00000031750 | Il34 |
| ENSMUSG00000039304 | Tnfsf10 | ENSMUSG00000026070 | Il18r1 |
| ENSMUSG00000037661 | Gpr160 | ENSMUSG00000026068 | Il18rap |
| ENSMUSG00000027665 | Pik3ca | ENSMUSG00000020009 | Ifngr1 |
| ENSMUSG00000074637 | Sox2 | ENSMUSG00000018341 | H12rb2 |
| ENSMUSG00000027793 | Ccna1 | ENSMUSG00000030167 | Klrc1 |
| ENSMUSG00000036362 | P2ry13 | ENSMUSG00000048521 | Cxcr6 |
| ENSMUSG00000028011 | Tdo2 | ENSMUSG00000013089 | Etv5 |
| ENSMUSG00000027995 | Tlr2 | ENSMUSG00000045991 | Onecut2 |
| ENSMUSG00000028076 | Cd1d1 | ENSMUSG00000059325 | Hopx |
| ENSMUSG00000004885 | Crabp2 | ENSMUSG00000025929 | Il17a |
| ENSMUSG00000027947 | Il6ra | ENSMUSG00000041872 | Il17f |
| ENSMUSG00000056054 | S100a8 | ENSMUSG00000004791 | Pgf |
| ENSMUSG00000056071 | S100a9 | ENSMUSG00000041324 | Inhba |
| ENSMUSG00000038642 | Ctss | ENSMUSG00000027718 | Il21 |
| ENSMUSG00000027878 | Notch2 | ENSMUSG00000010142 | Tnfrsf13b |
| ENSMUSG00000051076 | Vtcn1 | ENSMUSG00000022797 | Tfrc |
| ENSMUSG00000027863 | Cd2 | ENSMUSG00000027164 | Traf |
| ENSMUSG00000027852 | Nras | ENSMUSG00000027864 | Ptgfrn |
| ENSMUSG00000032902 | Skc1Ga1 | ENSMUSG00000019256 | Ahr |
| ENSMUSG00000027840 | Wnt2b | ENSMUSG00000021356 | Irf4 |
| ENSMUSG00000027966 | Col11a1 | ENSMUSG00000072889 | Nfxl1 |
| ENSMUSG00000027962 | Vcam1 | ENSMUSG00000032238 | Rora |
| ENSMUSG00000033377 | Palmd | ENSMUSG00000000869 | Il4 |
| ENSMUSG00000028017 | Egf | ENSMUSG00000031497 | Tnfsf13b |
| ENSMUSG00000028163 | Nfkb1 | ENSMUSG00000003420 | Fcgrt |
| ENSMUSG00000028268 | Gbp3 | ENSMUSG00000034266 | Batf |
| ENSMUSG00000040264 | Gbp2b | ENSMUSG00000056749 | Nfil3 |

TABLE 1-continued

Murine Pan-Cancer Gene Expression Panel for Immuno-Oncology and Tumor Microenvironment Study

| Ensemble ID | Gene | Ensemble ID | Gene |
|---|---|---|---|
| ENSMUSG00000028270 | Gbp2 | ENSMUSG00000024140 | Epas1 |
| ENSMUSG00000005034 | Prkacb | ENSMUSG00000024401 | Tnf |
| ENSMUSG00000028224 | Nbn | ENSMUSG00000037104 | Socs5 |
| ENSMUSG00000041135 | Ripk2 | ENSMUSG00000034855 | Cxcl10 |
| ENSMUSG00000028284 | Map3k7 | ENSMUSG00000048480 | Cxcr1 |
| ENSMUSG00000028444 | Cntfr | ENSMUSG00000026321 | Tnfrsf11a |
| ENSMUSG00000073889 | Il11ra1 | ENSMUSG00000023206 | Il15ra |
| ENSMUSG00000073888 | Ccl27a | ENSMUSG00000026942 | Traf2 |
| ENSMUSG00000071005 | Ccl19 | ENSMUSG00000060477 | Irak2 |
| ENSMUSG00000094686 | Ccl21a | ENSMUSG00000032012 | Nectin1 |
| ENSMUSG00000035683 | Melk | ENSMUSG00000025997 | Ikzf2 |
| ENSMUSG00000007613 | Tgfbr1 | ENSMUSG00000022528 | Hes1 |
| ENSMUSG00000028362 | Tnfsf8 | ENSMUSG00000003545 | Fosb |
| ENSMUSG00000095498 | Ifna1 | ENSMUSG00000072109 | A530040E14Rik |
| ENSMUSG00000044303 | Cdkn2a | ENSMUSG00000112023 | Lilr4b |
| ENSMUSG00000073802 | Cdkn2b | ENSMUSG00000112148 | Lilrb4a |
| ENSMUSG00000028530 | Jak1 | ENSMUSG00000029580 | Actb |
| ENSMUSG00000028518 | Prkaa2 | ENSMUSG00000061577 | Adgrg5 |
| ENSMUSG00000028716 | Pdzk1ip1 | ENSMUSG00000057666 | Gapdh |
| ENSMUSG00000028678 | Kif2c | ENSMUSG00000105646 | Gm30211 |
| ENSMUSG00000006398 | Cdc20 | ENSMUSG00000049932 | H2ax |
| ENSMUSG00000033191 | Tie1 | ENSMUSG00000069265 | H3c1 |
| ENSMUSG00000028645 | Slc2a1 | ENSMUSG00000062070 | Pgk1 |
| ENSMUSG00000042677 | Zc3h12a | ENSMUSG00000034487 | Poglut3 |
| ENSMUSG00000000409 | Lck | ENSMUSG00000071866 | Ppia |
| ENSMUSG00000028580 | Pum1 | ENSMUSG00000109713 | Pvrig |
| ENSMUSG00000007880 | Arid1a | ENSMUSG00000050379 | Septin6 |
| ENSMUSG00000037157 | Il22ra1 | ENSMUSG00000024349 | Sting1 |
| ENSMUSG00000036905 | C1qb | ENSMUSG00000022285 | Ywhaz |

What is claimed is:

1. A method for assessing immune response in a murine model, the method comprising:

obtaining a sample from the murine model;

detecting the expression level of a panel of genes in the sample, wherein the panel comprises 1080 genes as shown in Table 1;

comparing the expression level of the panel to a reference expression level; and assessing the immune response in the murine model.

2. The method of claim 1, wherein the sample is a cell, a tissue, an organoid, or a combination thereof.

3. The method of claim 1, wherein the murine model has a tumor.

4. The method of claim 1, wherein the sample is a tumor tissue.

5. The method of claim 1, wherein the murine model been treated with a therapy.

6. The method of claim 4, wherein the therapy is an immune therapy.

7. The method of claim 1, where the expression of the panel of genes is detected using next-generation sequencing (NGS).

8. The method of claim 1, wherein the immune response is assessed by determining the amount or activation of an immune cell in the sample, wherein the immune cell is selected from the group consisting of B-cell, dendritic cell, macrophage, monocyte, natural killer cell, CD4+ T cell and CD8+ T cell.

9. A method for evaluating a treatment in a murine model, comprise administering a treatment to a murine model;

obtaining a sample from the murine model;

detecting the expression level of a panel of genes in the sample, wherein the panel comprises 1080 genes as shown in Table 1;

comparing the expression level of the panel to a reference expression level; and evaluating the immune response in the murine model.

10. The method of claim 9, wherein the sample is a cell, a tissue, an organoid, or a combination thereof.

11. The method of claim 9, wherein the murine model has a tumor.

12. The method of claim 9, wherein the sample is a tumor tissue.

13. The method of claim 9, wherein the treatment is an immune treatment.

14. The method of claim 9, where the expression of the panel of genes is detected using NGS.

15. The method of claim 9, wherein the immune response is assessed by determining the amount or activation of an immune cell in the sample, wherein the immune cell is selected from the group consisting of B-cell, dendritic cell, macrophage, monocyte, natural killer cell, CD4+ T cell and CD8+ T cell.

16. A kit for assessing immune response in a murine model comprising primers for detecting the expression of a panel of genes in a sample from the murine model, wherein the panel comprises 1080 genes as shown in Table 1.

17. The kit of claim 16, wherein the sample is a cell, a tissue, an organoid, or a combination thereof.

18. The kit of claim 16, wherein the murine model has a tumor.

19. The kit of claim 16, wherein the sample is a tumor tissue.

20. The kit of claim 16, wherein the murine model been treated with a therapy.

21. The kit of claim 20, wherein the therapy is an immune therapy.

22. The kit of claim 16, wherein the immune response is assessed by determining the amount or activation of an immune cell in the sample, wherein the immune cell is selected from the group consisting of B-cell, dendritic cell, macrophage, monocyte, natural killer cell, CD4+ T cell and CD8+ T cell.

\* \* \* \* \*